US00PP29701P3

(12) United States Plant Patent
Olesen

(10) Patent No.: US PP29,701 P3
(45) Date of Patent: Sep. 25, 2018

(54) MINIATURE ROSE PLANT NAMED 'POULPAH086'

(50) Latin Name: ***Rosa* hybrid**
Varietal Denomination: Poulpah086

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensburg (DK)

( * ) Notice: Subject to any disclaimer, the term of this patent is extended or adjusted under 35 U.S.C. 154(b) by 0 days.

(21) Appl. No.: 15/330,289

(22) Filed: Sep. 6, 2016

(65) Prior Publication Data

US 2018/0070503 P1 Mar. 8, 2018

(51) Int. Cl.
*A01H 5/02* (2018.01)

(52) U.S. Cl.
USPC ..... Plt./121
CPC ..... *A01H 5/0222* (2013.01)

(58) Field of Classification Search
USPC ..... Plt./101, 116, 121
See application file for complete search history.

(56) References Cited

PUBLICATIONS

UPOV-PLUTO: Plant Variety Database, Oct. 20, 2017, citation for Poulpah086. 1 page.*
Poulsen—Outdoor Roses 2015. http://fliphtml5.com/kekq/iswp/basic. Accessed Oct. 20, 2017. 2 pages.*

* cited by examiner

*Primary Examiner* — Susan McCormick Ewoldt
*Assistant Examiner* — Karen M Redden

(57) ABSTRACT

A new garden rose plant of the Miniature class which has abundant, light pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulpah086'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpah086', originated as a single seedling from the stated cross.

The new variety may be distinguished from its male pollen parent and female seed parent primarily by the following characteristics. The male pollen parent plant has near white flowers, while the new plant has light pink flowers. The female seed parent plant has medium red flowers, while the new plant has light pink flowers.

The objective of the hybridization of this rose variety was to create a new and distinct variety for garden use with unique qualities, such as:

1. Uniform and abundant light pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah086' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpah086' was selected in the spring of 2011 by the inventor as a single plant from the progeny of the aforementioned hybridization.

Asexual reproduction of 'Poulpah086' by rooted cuttings was first done by Mogens N. Olesen in the nursery in Fredensborg, Denmark in July, 2011. This initial and other subsequent asexual propagations conducted in controlled environments have demonstrated that the characteristics of 'Poulpah086' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah086'.

Specifically illustrated in FIG. 1 of the drawings are an open flower, flower bud, petals detached, leaves, sepals detached, and reproductive flower parts.

Figure 1:
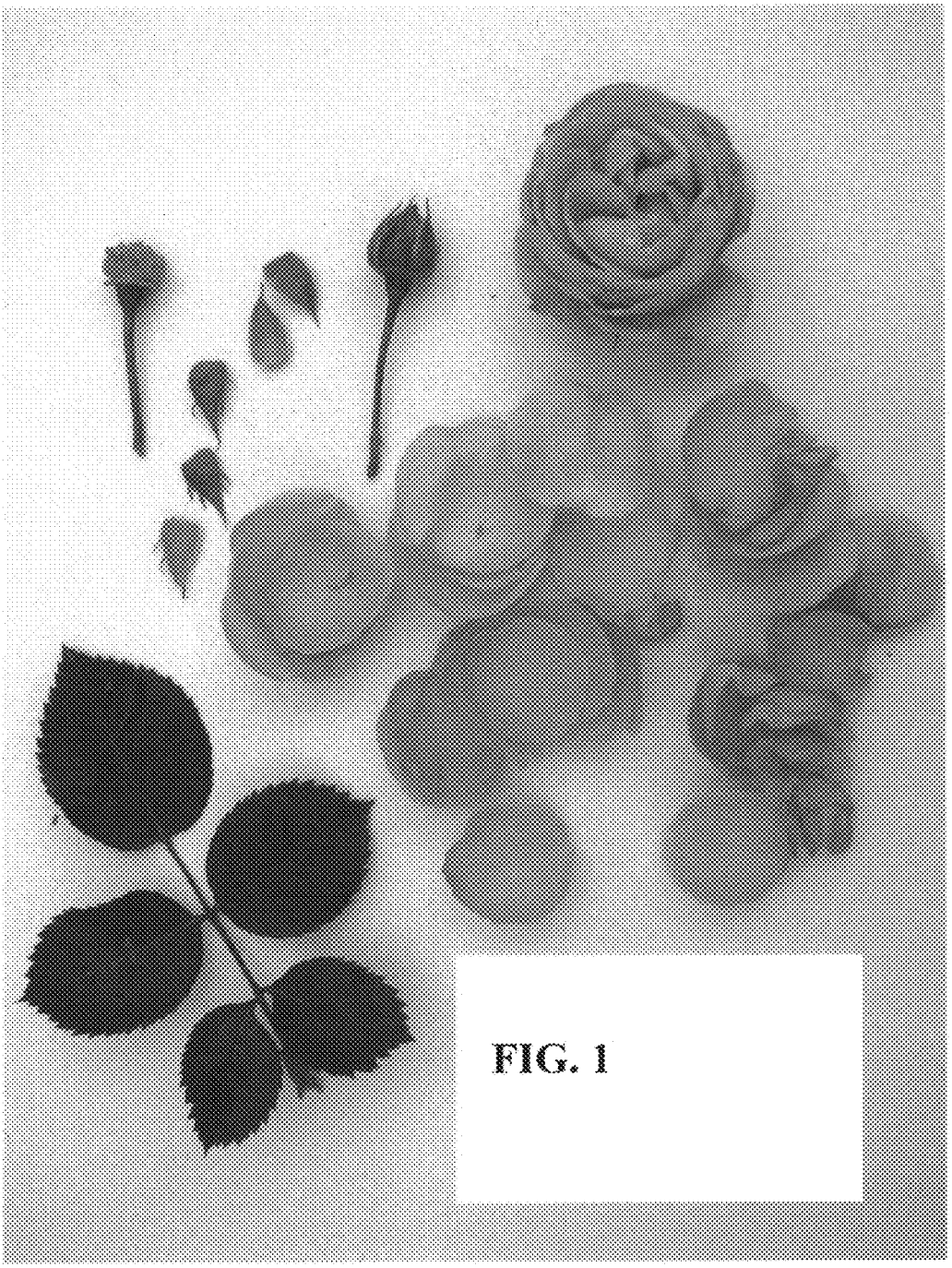
Figure 2:
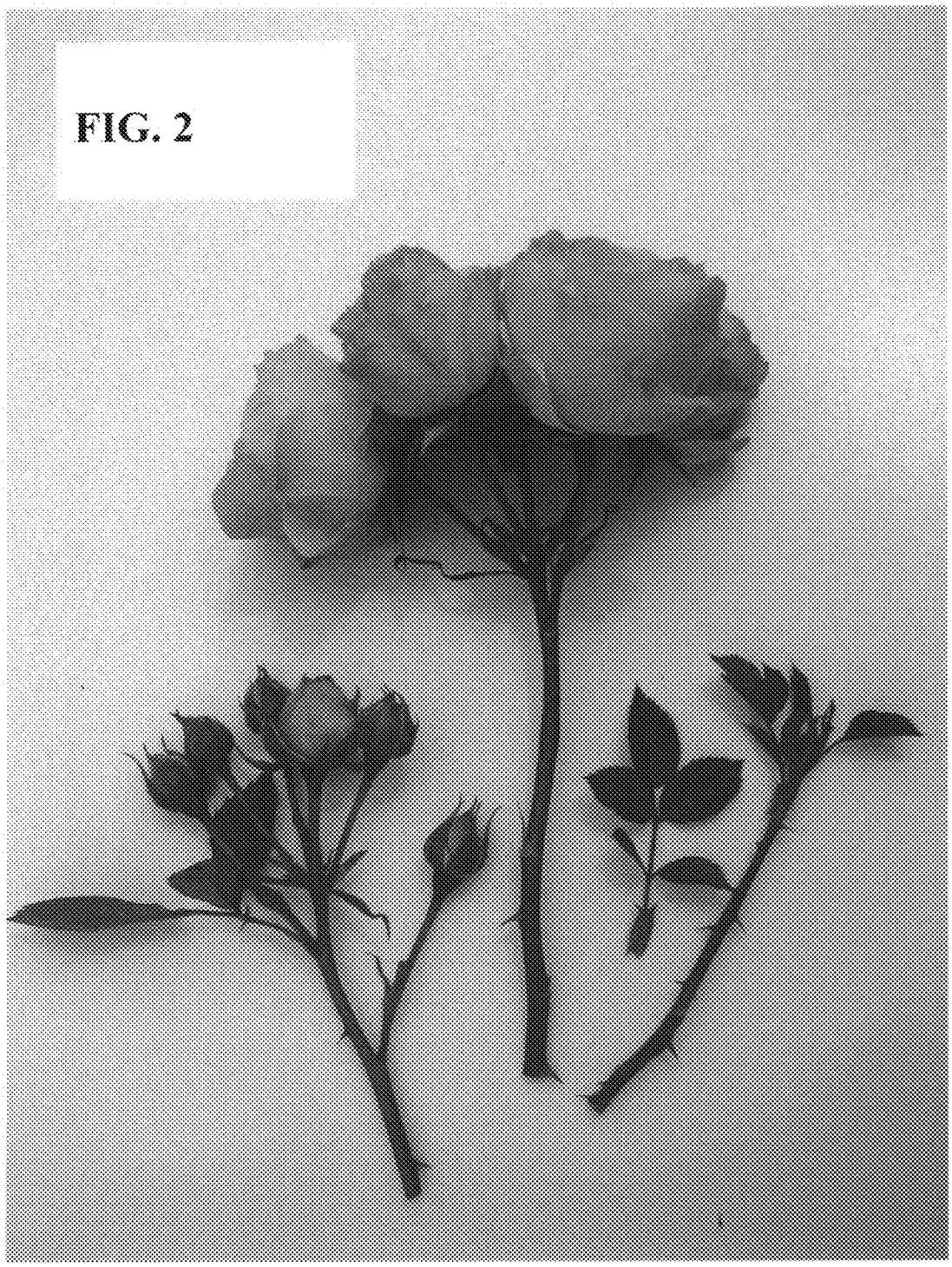

Illustrated in FIG. 2 are flowering branches at various stages of development with juvenile leaf and stem. Plants shown are 2 years of age.

DETAILED DESCRIPTION OF THE VARIETY

The following is a description of 'Poulpah086', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'POULhi008', U.S. Plant Pat. No. 15,722 are compared to 'Poulpah086' in Chart 1.

CHART 1

| | 'Poulpah086' | 'POULhi008' |
|---|---|---|
| Petal Count | 40 | 40 to 45 |
| Flower Diameter | 55 mm | 80 mm |
| General Tonality of Flower Color | Red-Purple Group 62A | Red Group 55B |

Flower and flower bud:

*Blooming habit.*—Continuous.

*Flower bud.*—Size: Upon opening, 25 mm in length from base of receptacle to end of bud. Bud diameter is 18 mm. Bud form: Globose. Bud color: As sepals divide petals are Red Group 43C, with intonations of Orange-Red Group 35D. Sepal inner surface: Color: Yellow-Green Group 147D. Surface: Lightly pubescent. Sepal outer surface: Color: Yellow-Green Group 144A with intonations of Greyed-Red Group 178C. Texture: Smooth. Sepal Shape: Apex: Cirrhose. Base: Flat at union with receptacle. Sepal Margin: Margins have moderate foliaceous appendages on three of the five sepals. Sepal size: 25 mm long, 12 mm wide. Receptacle: Texture: Smooth. Size: 8 mm in height, 5 mm wide. Color: Yellow-Green Group 144A. Shape: Campanulate. Pedicel: Surface: Smooth. Length: 30 to 35 mm. Diameter: 35 mm on average. Color: Yellow-Green Group 144A with intonations of Greyed-Red Group 179A. Strength: Strong.

*Flower bud development.*—Flower buds are borne in clusters of approximately 5 to 7 flower buds per stem in panicle form.

*Flower bloom.*—Fragrance: Moderate rose scent. Duration: The blooms have a duration on the plant of approximately 10 days. Petals fall cleanly away from plant after flowers have fully matured. Size: Flower diameter is 55 mm when open. Flower depth is 40 mm. Flower shape: Rosette, very double flower with many slightly overlapping petals of different sizes. Shape of flower, side view: The upper portion is flat. The lower portion is slightly concave.

*Petalage.*—Under normal conditions, flowers have 40 petals.

*General tonality of flower.*—Open flowers are Red-Purple Group 62A.

*Petal color.*—Upon opening, outer petals: Upper surface: Red Group 55C with intonations of Red Group 36A toward basal zone. Yellow Group 10B at petal base. Lower surface: Red-Purple Group 62C and Red-Purple Group 62D. Yellow Group 10C at petal base. Upon opening, inner petals: Upper surface: Red Group 55C with intonations of Red Group 36A toward basal zone. Yellow Group 10B at petal base. Lower surface: Red Group 49A with intonations of Red Group 36B. Yellow Group 10C at petal base. After opening, outer & inner petals Upper surface: Red Group 55C with intonations of Red Group 36A toward basal zone. Yellow Group 10B at petal base. Lower surface: Red-Purple Group 62C and Red-Purple Group 62D. Yellow Group 10C at petal base.

*Petals.*—Petal Reflex: Flat. Margin: Cleft at margin. Moderate undulations. Shape: Generally rounded. Apex shape: Rounded. Base shape: Rounded. Size: 40 mm (l)×42 mm (w). Texture: Smooth. Thickness: Average.

*Petaloids.*—Size: 15 mm (l) by 9 mm (w). Quantity: About 5. Shape: Irregular, with a rounded apex and acute base. Color: The upper surface is Red Group 55C with intonations of Red Group 36A toward basal zone. Yellow Group 10B at petaloid base. The lower surface is Red Group 49A with intonations of Red Group 36B. Yellow Group 10C at the petaloid base.

*Reproductive flower parts.*—Pollen: None observed. Anthers: Size: 2 mm in length. Color: Orange Group 26A. Quantity: 35 on average. Filaments: Color: Yellow-Orange Group 15A. Length: 6 mm. Pistils: Length: 10 mm. Quantity: 30 on average. Stigmas: Color: Yellow-Green Group 154D. Styles: Color: Yellow-Green Group 154D. Location of stigmas: Superior in location relative to the length of the filaments and the height of the anthers. Hips: None Observed.

Plant:

*Plant growth.*—Upright. Plants are about 40 cm in height, and 37 cm wide.

*Stems.*—Color: Juvenile growth: Yellow-Green Group 144B. Mature growth: Yellow-Green Group 144A. Length: On average, canes are 18 cm from the base of the plant to the flowering portion. Diameter: 6 mm. Internodes: On mature canes about 35 mm between nodes. Surface Texture: Young wood: Smooth. Older wood: Smooth.

*Long prickles.*—Incidence: 5 prickles per 10 cm of stem. Size: Average length of prickles on mature stems is 9 mm. Shape: Upper portion is linear. Lower portion is concave. Color: Juvenile prickles: Greyed-Red Group 178A. Mature prickles: Greyed-Orange Group 171A and Greyed-Yellow Group 162A.

*Plant foliage.*—Compound leaf: 140 mm (l)×110 (w). Quantity: 2 leaves per 10 cm of stem on average. Leaf bearing angle to the stem: 45 degrees. Color of juvenile foliage: Upper side: Yellow-Green Group 146A with intonations of Greyed-Purple Group 183A at the margins. Lower side: Yellow-Green Group 144A. Color of mature foliage: Upper side: Yellow-Green Group 146A. Lower side: Yellow-Green Group 146B.

*Plant leaves and leaflets.*—Stipules: Size: 18 mm long, 2 mm wide. Quantity: 2 per compound leaf. Shape: Linear, slightly broad based with outward extending apices. Margins: Finely serrated. Color: Yellow-Green Group 144A. Petiole: Length: About 32 mm. Diameter: 2 mm. Upper surface: Color: Yellow-Green Group 144A. Lower surface: Color: Yellow-Green Group 144A. Rachis: Length: About 50 mm. Upper surface: Color: Yellow-Green Group 144A. Lower surface: Color: Yellow-Green Group 144A. Leaflet: Quantity: Normally 5 leaflets. Margins: Serrated. Size: On average terminal leaflets are 60 mm long, 45 mm wide. Shape: Generally elliptical. Base: Rounded. Apex: Cuspidate. Texture: Smooth. Thickness: Average. Arrangement: Odd pinnate. Venation: Reticulate. Glossiness: Not glossy.

*Disease resistance.*—Above average resistance to powdery mildew *Sphaerotheca pannosa,* downy mildew *Peronospora sparsa,* rust *Phragmidium* spp. Average resistance to black spot *Diplocarpon rosae,* and *Botrytis cinerea.*

*Cold hardiness.*—The variety is tolerant to USDA Cold Hardiness Zone 6.

*Heat tolerance.*—The variety has been found to be suitable for climate conditions found in the American Horticulture Society heat zone 7.

I claim:

1. A new and distinct variety of rose plant of the Miniature rose class named 'Poulpah086', substantially as illustrated and described herein, due to its abundant light pink flowers, disease resistance, and extended period of bloom.

* * * * *